United States Patent [19]
Rosenblood et al.

[11] Patent Number: 5,868,769
[45] Date of Patent: Feb. 9, 1999

[54] TONGUE SCRAPER

[75] Inventors: Kenneth L. Rosenblood; Robert G. Hayman, both of Los Angeles, Calif.

[73] Assignee: Discus Dental Impressions, Inc., Culver City, Calif.

[21] Appl. No.: 917,245

[22] Filed: Aug. 25, 1997

[51] Int. Cl.$^6$ .............................. A61B 17/24; A61F 9/00
[52] U.S. Cl. .......................... 606/161; 606/161; 15/111; 15/176.1; 15/176.4; 15/176.5; 15/176.6
[58] Field of Search ................ 606/161; 15/111, 15/176.1, 176.4, 176.5, 176.6

[56] References Cited

U.S. PATENT DOCUMENTS

| | | | |
|---|---|---|---|
| 1,893,524 | 1/1933 | Shanley | 606/161 |
| 5,005,246 | 4/1991 | Yen-Hui | 606/161 |
| 5,217,475 | 6/1993 | Kuber . | |

FOREIGN PATENT DOCUMENTS 2568-465-A  8/1984  France ................... 606/161

*Primary Examiner*—Michael P. Buiz
*Assistant Examiner*—Vy Quang Bui
*Attorney, Agent, or Firm*—Christie, Parker & Hale, LLP

[57] ABSTRACT

A tongue scraper having a convex-shaped edge and a linear edge. The convex-shaped edge conforms to the lateral concavity of the tongue. The linear edge conforms to planar areas of the tongue. Tight gripping of the scraper is facilitated by a hole at each end intended to be pinched between the thumb and finger. In a first embodiment the scraper includes serrations on the convex and linear edges. In a second embodiment the convex and linear edges are smooth.

4 Claims, 2 Drawing Sheets

TONGUE SCRAPER

BACKGROUND OF THE INVENTION

1. Field of the Invention

The present invention relates to devices for promoting dental hygiene, and more particularly to a tongue scraper for cleansing food debris, volatile sulfur compounds, dead cells, microflora and other microorganisms from the tongue.

2. Description of the Related Art

The human tongue is slightly furry in texture and has numerous protuberances (viz., papillae) which convey to the brain the senses of taste and touch. Consequently, the tongue easily can become a breeding ground for microflora such as bacteria, as well as a repository for food debris, volatile sulfur compounds which are a major cause of halitosis, and dead cells. Over time, some of the collected material becomes a soft plaque which is another cause of bad breath, and also attacks the teeth and gums. Tests have shown that daily scraping to reduce the amount of coating on the tongue eliminates much of the bacteria and sulfur compounds, significantly inhibiting plaque formation on the teeth in the long term, and substantially reducing halitosis in the short term.

A wide variety of tongue scrapers are known in the dental hygiene arts. For example, U.S. Pat. No. 3,477,435 to Artelli discloses a tongue scraper with a metal blade-like member having one end portion formed to fit between wooden handle parts. A rigid blade-like portion extends forwardly of the handle at the other end in a curve for a right-handed or left-handed person. U.S. Pat. No. 3,890,964 to Castanedo discloses a one-piece tongue scraper which includes an elongated handle at one end with longitudinally diverging arms at the other end. The ends of the arms are connected by a longitudinally bowed cross bar having a laterally centered arched portion and beveled edge faces. U.S. Pat. No. 4,455,704 to Williams discloses a tongue cleaner in combination with a toothbrush. The tongue cleaner is an arcuate scraper member which is centrally secured to the tooth brush handle at the end opposite the brush.

U.S. Pat. No. 5,217,475 ("'475") to Kuber discloses a tongue scraper intended to be disposable after being used only once. The normally planar scraper is formed of a flexible, resilient material and includes opposed outer portions having smooth generally parallel edges. Each outer portion terminates in a rounded free end portion. An elongated central portion having a concave serrated edge is disposed between the two outer portions. Holding one end portion firmly in each hand and bending the scraper into a U-shape, the user contacts the extended tongue with the serrated edge and then scrapes gently from back to front to remove accumulated coating material.

The concave edge of the '475 scraper cannot optimally engage the tongue's lateral concavity. The mismatch between the two concavely arcuate conformations creates coverage gaps resulting in inefficient cleansing. What is needed is a scraper which includes an edge having a convexly shaped contour which conforms to the tongue's concave contour, and a linear edge to efficiently scrape the tongue's planar surface portions.

OBJECTS OF THE INVENTION

Accordingly, it is an object of the present invention to provide a simple, convenient tongue scraper having an edge which conforms to the tongue's lateral contour.

Another object of the invention is to provide a tongue scraper having an edge which conforms to the tongue's planar areas.

A further object of the invention is to provide a tongue scraper that is inexpensive to manufacture.

Other objects of the invention will become evident when the following description is considered with the accompanying drawing figures. In the figures and description, numerals indicate the various features of the invention, like numerals referring to like features throughout both the drawings and the description.

SUMMARY OF THE INVENTION

These and other objects are achieved by the present invention which in a first aspect provides a tongue scraper including opposed generally planar end portions each having a hole, and a generally planar central portion disposed between the end portions. The central portion is bounded longitudinally by a convexly arcuate edge and a generally linear edge. In a first embodiment, a multiplicity of serrations on the convex edge are used to scrape the lateral concavity of the tongue upper surface, and a multiplicity of serrations on the linear edge are used to scrape planar areas of the tongue upper surface. In a second embodiment, the convex and linear edges both have a smooth surface. The hole in each end portion allows the user to firmly grip the end portions between thumb and finger.

In another aspect the invention provides a tongue scraper fabricated from a resilient material and including opposed generally planar end portions each terminating in a generally elliptical arcuate edge and extending proximally in a neck having arcuate edges tapering to a predetermined width. The edges each have a plurality of serrations, and the end portions each have a hole. The tongue scraper further includes a generally planar central portion disposed symmetrically between and contiguous to the tapered neck of each end portion. The central portion is determined longitudinally by a convexly arcuate edge having a multiplicity of serrations, and a generally linear edge having a multiplicity of serrations.

In yet another aspect the invention provides a tongue scraper fabricated from a resilient material and including opposed generally planar end portions each terminating in a generally elliptical arcuate edge and extending proximally in a neck having arcuate edges tapering to a predetermined width. The edges each have a smooth surface, and the end portions each have a hole. The tongue scraper further includes a generally planar central portion disposed symmetrically between and contiguous to the tapered neck of each end portion. The central portion is determined longitudinally by a convexly arcuate edge having a smooth surface, and a generally linear edge having a smooth surface.

A more complete understanding of the present invention and other objects, aspects and advantages thereof will be gained from a consideration of the following description of the preferred embodiment read in conjunction with the accompanying drawings provided herein.

DESCRIPTION OF THE PREFERRED EMBODIMENTS

Figure 1:
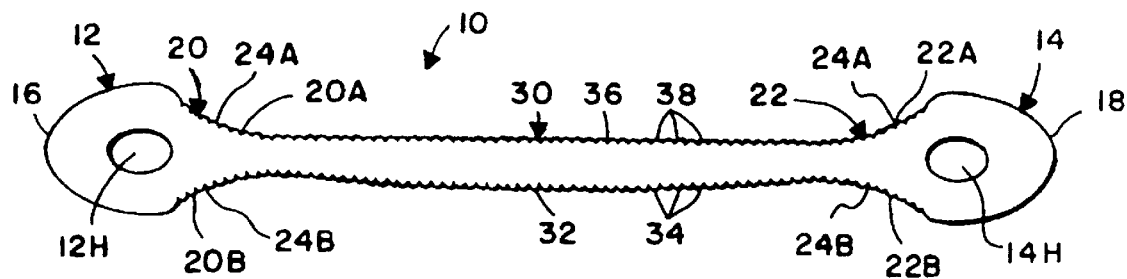
FIG. 1 is a plan view of a first embodiment of a tongue scraper according to the invention, including a central portion having a convex first edge and a linear second edge, each with a multiplicity of serrations.

While the present invention is open to various modifications and alternative constructions, the preferred embodiments shown in the drawings will be described herein in detail. It is to be understood, however, there is no intention to limit the invention to the particular forms disclosed. On the contrary, it is intended that the invention cover all modifications, equivalences and alternative constructions falling within the spirit and scope of the invention as expressed in the appended claims.

Figure 2:
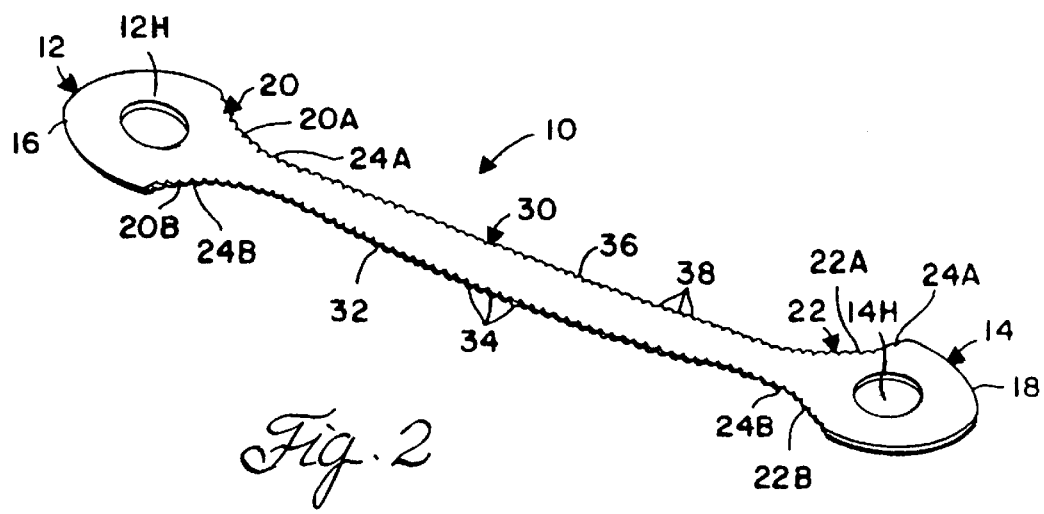
FIG. 2 is a perspective view of the FIG. 1 tongue scraper.

Referring to FIGS. 1 and 2, a first embodiment of a tongue scraper 10 adapted for scraping coating material such as food debris, volatile sulfur compounds, dead cells and microflora from the upper surface of a tongue includes opposed first and second generally planar end portions 12, 14, each terminating distally in a generally elliptical arcuate edge 16, 18, respectively, and each having therethrough a hole 12H, 14H, respectively. End portions 12, 14 extend proximally in a neck 20, 22, respectively, each neck having first and second arcuate edges 20A, 20B and 22A, 22B, respectively, tapering to a predetermined width. Edges 20A, 22A and 20B, 22B have a common plurality of serrations 24A, 24B, respectively. The tongue scraper 10 further includes a generally planar central portion 30 disposed symmetrically between and smoothly contiguous to end portion necks 20 and 22. Central portion 30 is determined longitudinally by a convexly arcuate first edge 32 having a multiplicity of serrations 34, and a generally linear second edge 36 having a multiplicity of serrations 38.

Figure 3:
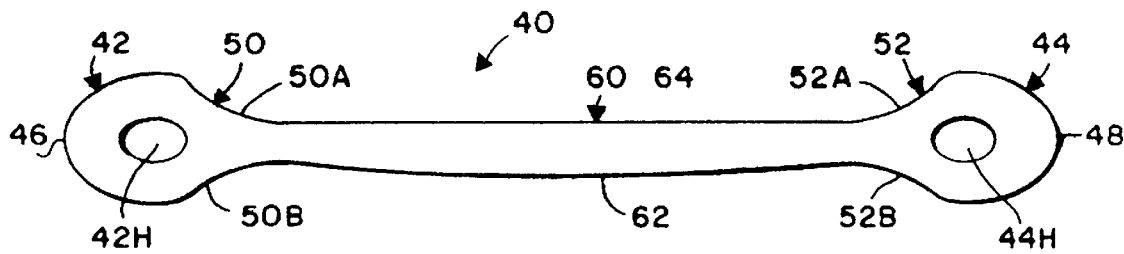
FIG. 3 is a plan view of a second embodiment of a tongue scraper according to the invention, including a central portion having smooth convex and linear edges.
Figure 4:
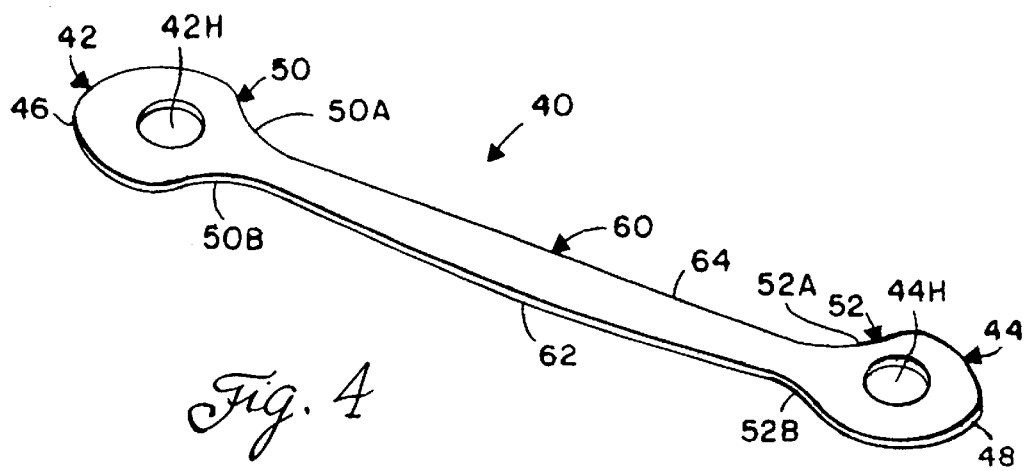
FIG. 4 is a perspective view of the FIG. 3 tongue scraper.

Referring to FIGS. 3 and 4, a second embodiment of a tongue scraper 40 includes opposed first and second generally planar end portions 42, 44, each terminating distally in a generally elliptical arcuate edge 46, 48, respectively, and each having therethrough a hole 42H, 44H, respectively. End portions 42, 44 extend proximally in a neck 50, 52, respectively, each neck having first and second arcuate edges 50A, 50B and 52A, 52B, respectively, tapering to a predetermined width. Edges 50A, 52A and 50B, 52B each have a smooth surface. The tongue scraper 40 further includes a generally planar central portion 60 disposed symmetrically between and smoothly contiguous to end portion necks 50 and 52. Central portion 60 is determined longitudinally by a convexly arcuate first edge 62 having a smooth surface, and a generally linear second edge 64 having a smooth surface.

Tongue scrapers 10 and 40 are fabricated from a resilient material so that if central portion 30 or 60 is bent into an arc, the scraper immediately will return to its normally planar state once the end portions are released.

Preferably, the tongue scrapers are fabricated by die-cutting PROPRINT™, a soft extruded mineral-filled polypropylene.

In use, the end portions 12, 14 or 42, 44 are grasped between the thumb and forefinger or middle finger. Holes 12H, 14H and 42H, 44H facilitate gripping so that central portion 30 or 60, respectively, can be maintained under tight control. The user has the option of either bending the central portion into an arc or keeping it planar. He or she then brings the convexly arcuate edge or linear edge into contact with the extended tongue, depending on whether a concave portion or a planar portion is to be cleansed, and scrapes gently from back to front to remove the coating material.

What is claimed is:

1. A tongue scraper for scraping coating material from the upper surface of a human tongue, comprising:

opposing first and second generally planar end portions each having a hole therethrough, a generally planar central portion disposed between the end portions and extended from the first end portion to the second end portion, the central portion determined longitudinally by a first edge having a convexly arcuate shape that extends the full length of the central portion and by a generally linear second edge extending the full length of the central portion;

scraping means for conforming to the lateral concavity of said tongue upper surface, wherein said scraping means comprises a first multiplicity of serrations on said first edge;

scraping means for conforming to generally planar areas of said tongue upper surface, wherein said scraping means comprises a second multiplicity of serrations on said second edge; and gripping means for holding the scraper between the thumb and a finger during use wherein said gripping means comprises the hole in each end portion.

2. A tongue scraper for scraping coating material from the upper surface of a human tongue, comprising:

opposed first and second generally planar end portions, the end portions each terminating distally in a generally elliptical arcuate edge and extending proximally in a neck having first and second arcuate edges tapering to a predetermined width, the first edges each having a first plurality of serrations, the second edges each having a second plurality of serrations, the end portions each having a hole therethrough; and a generally planar central portion disposed symmetrically between the end portions and extended from the tapered neck of the first end portion to the tapered neck of the second end portion, the central portion determined longitudinally by a first edge having a convexly arcuate shape that extends the full length of the central portion and provided with a first multiplicity of serrations, and a generally linear second edge with a second multiplicity of serrations.

3. The tongue scraper of claim 2, wherein the scraper is fabricated from a resilient material.

4. The tongue scraper of claim 3, wherein said material is an extruded mineral-filled polypropylene.

* * * * *